(12) United States Patent
Powell (10) Patent No.: US 7,534,225 B2
(45) Date of Patent: May 19, 2009

(54) DEGASSING METHOD AND SYSTEM

(75) Inventor: David G. Powell, Pasadena, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1016 days.

(21) Appl. No.: 10/638,086

(22) Filed: Aug. 7, 2003

(65) Prior Publication Data

US 2005/0033231 A1   Feb. 10, 2005

(51) Int. Cl.
*A61M 1/00* (2006.01)
(52) U.S. Cl. .................. 604/122; 604/125; 604/181
(58) Field of Classification Search ......... 604/124–125, 604/122, 118, 218–221, 139, 200–201, 203–205, 604/87, 148, 227–228
See application file for complete search history.

(56) References Cited

U.S. PATENT DOCUMENTS 1,039,591 A * 9/1912 Prideaux .................... 604/135
4,711,250 A * 12/1987 Gilbaugh et al. ............ 600/578
5,350,365 A * 9/1994 De Godoy Moreira ...... 604/187

\* cited by examiner

*Primary Examiner*—Nicholas D Lucchesi
*Assistant Examiner*—Theodore J Stigell
(74) *Attorney, Agent, or Firm*—Foley & Lardner LLP (57) ABSTRACT

A system and method for degassing a fluid in a syringe comprising and inserting the fluid into a negative pressure device. The system may include a holder for holding the syringe; a guide affixed to the holder; a slide for holding a plunger of the syringe, the slide being movably attached to the guide; and a locking mechanism opposite the holder for maintaining a position of the slide. The fluid degasses when the locking mechanism maintains the position of the slide. The system may also include a piercing element adjacent the holder for piercing the syringe. The system and method may also be used for removing fluid from a negative pressure device.

46 Claims, 6 Drawing Sheets

Fig. 6b

DEGASSING METHOD AND SYSTEM

BACKGROUND

1. Field of the Invention

Embodiments of the present invention relate to degassing methods and systems and, in particular, to methods and systems for degassing a fluid disposed in a standard syringe and for inserting a degassed fluid into a negative pressure device, such as, for example, a pump or other reservoir.

2. Description of Related Art

The use of implantable, fluid-delivering devices in the treatment of various medical conditions has necessitated requisite procedures for filling the devices with an appropriate fluid and removing "stale" fluid from the devices when necessary. Although the devices themselves, such as, for example, pumps and other reservoirs, could be surgically removed from a patient every time the addition or removal of fluid from the device is required, such an invasive surgical procedure performed multiple times would prove traumatic and debilitating to the patient. Furthermore, these types of procedures are time-consuming and expensive.

Implantable pumps and other fluid-containing reservoirs that are implanted into the human body typically operate as either a positive pressure device or a negative pressure device. Negative pressure devices have the advantage of precluding the fluid contained in the device from leaking into the body in the event the integrity of the seals of the device are compromised. Because the pressure in the pump or reservoir under which the fluid resides is negative with respect to the body, fluid would normally flow into the pump or reservoir rather than outward from the device and into the body should a break in the seals occur. Thus, a negative pressure device provides an element of safety for the patient, preventing a large, possibly toxic exposure to the fluid in the device if the seals of the device become compromised.

Filling an implanted, negative pressure device has typically been a two-step procedure. First, the fluid with which the device is to be filled is degassed. Without proper degassing, gasses that have been dissolved in the fluid could resurface as bubbles in the fluid when the fluid reaches the body, a situation that could be dangerous for the patient. Second, after degassing, the degassed fluid is inserted into the patient. This is typically done through the skin using a needle that interfaces with a port on the device.

The tools that have been available for the degas and fill procedure have been inadequate for efficiently accomplishing the procedure. For example, generally, the implant fluid is drawn into a syringe and degassed by pulling a vacuum in the syringe; however, no tool currently exists that that locks the plunger of the syringe in place once the plunger has been drawn back to create the vacuum. Thus, rather than being able to use standard, off-the-shelf syringes, prior art solutions have had to custom-modify parts of the syringe and use other external parts to lock the plunger of the syringe in place once a vacuum has been pulled. This type of solution is time-consuming, expensive and inefficient.

Also, both positive and negative pressure implant devices present challenges to the fill (or refill) procedure. In a positive pressure device, the fluid in the syringe must be at a greater pressure than the pressure existing in the device. Accordingly, the syringe used must be able to accommodate a pressure-generating apparatus to build up a presser in the barrel of the syringe.

In a negative pressure device, the fluid in the syringe will generally flow from the syringe to the device, since the pressure in the syringe is normally greater than the pressure in the device. However, under certain conditions, the pressure in the syringe may not be sufficiently greater than the pressure in the device to force the fluid to flow from the syringe to the device. In this situation, some type of mechanism must be used to generate enough pressure against the fluid in the syringe to cause the fluid to flow from the syringe into the device.

SUMMARY

It is therefore an object of embodiments of the present invention to provide a system and method for degassing a fluid in a syringe. It is a further object of embodiments of the present invention to provide a system and method for injecting a fluid into an implanted negative pressure device. It is yet a further object of embodiments of the present invention to provide a system and method for removing a fluid from an implanted negative pressure device.

A system for degassing a fluid in a syringe may include a holder for holding the syringe; a guide affixed to the holder; a slide for holding a plunger of the syringe; and a locking mechanism opposite the holder for maintaining a position of the slide. The slide may be movably attached to the guide and the fluid may degas when the locking mechanism maintains the position of the slide. The holder may be substantially circular and may accept a barrel of the syringe. The size of the holder may be adjustable.

The guide may be a cylindrical post. The guide may include a first post and a second post. The guide may include a single post. The slide may rotate about the single post. The slide may include a first aperture for accepting a plunger of the syringe; a second aperture adjacent the first aperture; a third aperture on a first side of the slide for accepting a first post; and a fourth aperture opposite the third aperture for accepting a second post.

The slide may also include a first aperture for accepting a plunger of the syringe; a second aperture adjacent the first aperture; a third aperture on a first side of the slide for accepting the first post; and a fourth aperture opposite the third aperture for accepting the second post. The slide may further include a latch for engaging the locking mechanism. Also, a size of the slide may be adjustable.

The locking mechanism may be spring loaded. Also, the system may include a piercing element adjacent the holder for piercing the syringe. The system may further include a lever hingedly attached to the holder. The piercing element may be affixed to the lever. A rotational movement of the lever may force the piercing element into the syringe. The piercing element may be movably attached to the holder. A force applied to the piercing element may force the piercing element into the syringe. The piercing element may peel away a portion of the syringe when the piercing element is forced into the syringe. The piercing element may pierce the syringe in a manner that precludes pieces of the syringe from separating from the syringe.

A degassing tool for degassing a fluid in a syringe may include a holder for holding the syringe; a guide affixed to the holder; a slide for holding and moving a plunger of the syringe; and a piercing element adjacent the holder for piercing the syringe. The slide may be movably attached to the guide.

The piercing element may be affixed to a lever. The lever being affixed to the holder. A rotational movement of the lever may force the piercing element into the syringe. The piercing element may also be movably attached to the holder. A force applied to the piercing element may the piercing element into the syringe. The piercing element may pierce the syringe in a manner that precludes pieces of the syringe from separating from the syringe.

The degassing tool may also include a locking mechanism disposed opposite the holder for maintaining a position of the slide. The locking mechanism may be spring loaded.

A method for degassing a fluid may include inserting a syringe into a degassing tool; drawing a fluid into the syringe; closing the syringe; retracting a plunger of the syringe to create a vacuum in a portion of a barrel of the syringe; locking the plunger using the degassing tool; expelling gas dissolved in the fluid into the vacuum in the portion of the syringe; and expelling the gas in the vacuum out of the syringe. The fluid may be insulin.

The syringe may be closed with a stopcock. The plunger may be disposed in a slidable portion of the degassing tool.

Expelling a gas dissolved in the fluid into the vacuum in the portion of the syringe may include shaking the syringe while the syringe may be disposed in the degassing tool. Expelling the gas in the vacuum out of the syringe may include opening the stopcock.

A method for degassing a fluid and inserting the fluid into a negative pressure device implanted in a patient may include inserting a syringe into a degassing tool; drawing a fluid into the syringe; closing the syringe; retracting a plunger of the syringe to create a vacuum in a portion of a barrel of the syringe; locking the plunger using the degassing tool; expelling gas dissolved in the fluid into the vacuum in the portion of the syringe; expelling the gas in the vacuum out of the syringe; inserting the syringe into the negative pressure device; and opening the syringe. The fluid may be insulin and the plunger may be disposed in a slidable portion of the degassing tool.

Expelling gas dissolved in the fluid into the vacuum in the portion of the syringe may include shaking the syringe while the syringe may be disposed in the degassing tool.

The method may further include piercing a portion of the barrel of the syringe. The portion of the barrel of the syringe pierced may be adjacent the fluid and opposite the implanted device. The barrel of the syringe may be pierced such that no pieces of the barrel dislodge into the fluid.

A method for filling a negative pressure device may include inserting a syringe into a degassing tool; closing the syringe; retracting a plunger of the syringe to create a vacuum in a portion of a barrel of the syringe; locking the plunger using the degassing tool; inserting the syringe into the negative pressure device; and opening the syringe. Also, the syringe may be inserted into the negative pressure device using a needle.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Although the following description is directed primarily toward a degassing system and method, embodiments of the present invention may be used in a variety of capacities and applications. For example, embodiments of the present invention may be used for degassing insulin or other medications. Also, embodiments of the present invention may be used to insert fluid, such as insulin or other medications, for example, into an implanted pump for delivery to patient. Embodiments of the present invention may also be used to remove fluid from an implanted negative pressure device, such as, for example, a pump or other reservoir. Generally, embodiments of the present invention may be adapted for use in any type of situation that calls for degassing a fluid, inserting the fluid into an implanted negative pressure device, or removing fluid from an implanted negative pressure device.

Figure 1:
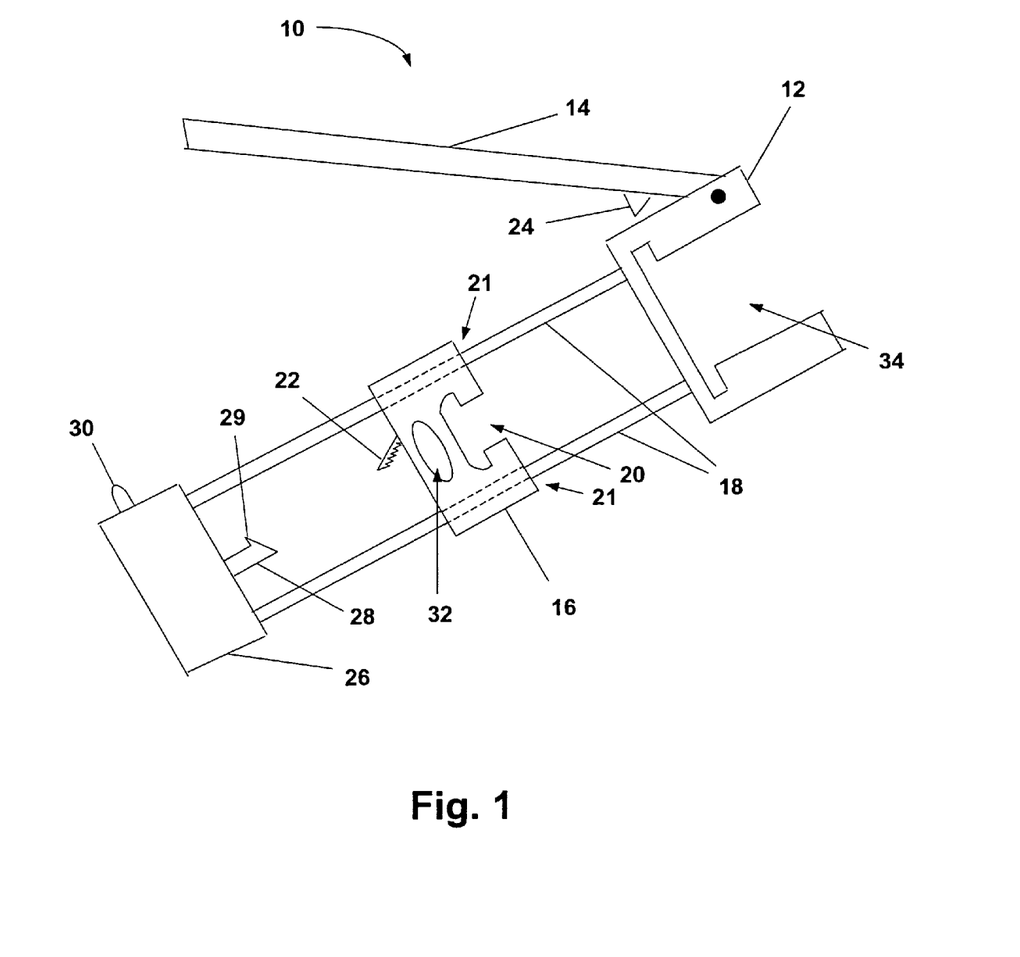
FIG. 1 shows a generalized view of a degassing tool according to an embodiment of the present invention.

A degassing tool 10 according to an embodiment of the present invention is shown in FIG. 1. The degassing tool 10 includes, but it is not limited to, a holder 12 for holding the barrel of a syringe containing fluid and a slide 16 that accepts a plunger of the syringe. The slide 16 may be movable along guides 18 that are affixed to the holder 12. The degassing tool 10 may also include, but is not limited to, a locking mechanism 28 for attaching to a latch 22 attached to the slide 16 and, thus, maintaining the slide 16 in a locked position. The locking mechanism 28 may be attached to a base 26 and may release the latch 22 by depressing a release button 30.

According to the embodiment of the invention shown in FIG. 1, the degassing tool 10 may also include a lever 14 that is hingedly or otherwise affixed to the holder 12. Affixed to the lever 14 is a piercing element 24.

According to embodiments of the present invention, the holder 12 may be formed into a variety of sizes and shapes. For example, the holder 12 may be in the form of a cylinder, a hexagon, an octagon, or even a square or a rectangle. According to an embodiment of the present invention, the holder 12 may be a simple ring.

In addition, the holder 12 may include a holder aperture 34. The holder aperture 34 may be sized such that it accepts the barrels of standard, off-the-shelf syringes that are common in the industry. The holder 12 may be designed such that a distance is maintained between the syringe and the plunger adequate to hold sufficient vacuum for degassing when the plunger is pulled away from the holder 12 and locked by the locking mechanism 28.

The slide 16 may also be formed into a variety of the shapes and sizes. The slide 16 may include a plunger aperture 20 that is sized to accept the plunger of the syringe that is in the holder 12. The slide 16 may also a include a handle aperture 32. The handle aperture 32 may be used for leverage when sliding the slide 16 away from the holder 12. For example, a user may insert his or her fingers into the handle aperture 32 while resting his or her palm on the base 26 to obtain leverage when pulling the plunger, which is located in the plunger aperture 20, away from the barrel of the syringe which is being held by the holder 12.

The slide 16 may also include guide apertures 21 that accept the guides 18 and along which the slide 16 may move.

The slide apertures 21 should be sized such that the slide 16 may move freely along the guides 18, which themselves may be formed, for example, as circular posts.

Although in the embodiment of the invention shown in FIG. 1, the slide 16 has been designed to accommodate two guides 18, the slide 16 may be designed to accommodate a variety of guide configurations. For example, according to an embodiment of the present invention, only one guide may be affixed to the holder 12 and the base 26. The slide 16 may be designed with only one guide aperture such that the slide is able to move up and down the length of the guide and may also rotate freely about the guide. In this configuration, a syringe may be placed into the holder 12 and the slide may be rotated about the guide to meet the plunger of the syringe.

The slide 16 may be designed in a variety of ways. For example, the slide 16 need not be a rigid member. The slide 16 may be designed, for example, as a wire that attaches to the plunger of the syringe.

The locking mechanism 28 may include any mechanism that can maintain the slide 16 in a fixed position after the plunger of the syringe has been pulled away from the holder 12 so that a vacuum forms within the interior of the syringe barrel. In the embodiment of the invention shown in FIG. 1, the locking mechanism 28 is a spring-loaded post that includes an extension 29 for mating with the latch 22. The latch 22 may include one or more teeth to provide a variable lock position for the slide 16. To release the latch 22 from the locking mechanism 28, a release button 30 may be depressed to move the locking mechanism 28 away from the teeth of the latch 22. According to another embodiment of the present invention, the locking mechanism 28 itself may be directly pushed away from the latch 22.

The lever 14 may simply be hinged to the holder 12 or may be spring-loaded, for example. The lever 14 may be operated such that rotation of the lever 14 forces the piercing element 24 into the barrel of a syringe that is positioned in the holder 12, thereby puncturing the barrel of the syringe and creating an opening for venting. The lever 14 may be designed with a cam or a screw, such that turning the cam or screw would force the lever 14 toward the syringe and cause the piercing element 24 to enter the syringe.

According to another embodiment of the present invention, the piercing element 24 may be located directly on the holder 12 and may be used to pierce the barrel of a syringe positioned in the holder 12 simply by pushing on the piercing element 24 itself. The piercing element 24 may also be designed with a cam or a screw, such that turning the cam or screw would force the piercing element 24 toward the syringe and cause the piercing element 24 to enter the syringe.

The piercing element 24 may be positioned in a variety of places on the lever 14 or the holder 12. According to an embodiment of the present invention, the piercing element 24 enters the syringe below the plunger cap but substantially close to the plunger cap so that use of the barrel of the plunger is maximized if the syringe is pierced by the piercing element 24.

The piercing element 24 may be designed such that there are no loose pieces of the syringe resulting from the piercing element 24 being forced into the syringe. Rather, when the piercing element 24 enters the syringe, the syringe remains intact. According to an embodiment of the present invention, the piercing element 24 may be designed to "enter and scoop." According to another embodiment of the present invention, the piercing element 24 may be designed to "peel away" a portion of the syringe. In other words, the piercing element 24 enters the syringe and scoops away a portion of the syringe so that loose pieces of the syringe due not fall into or contaminate the fluid in the barrel of the syringe.

Figure 2:
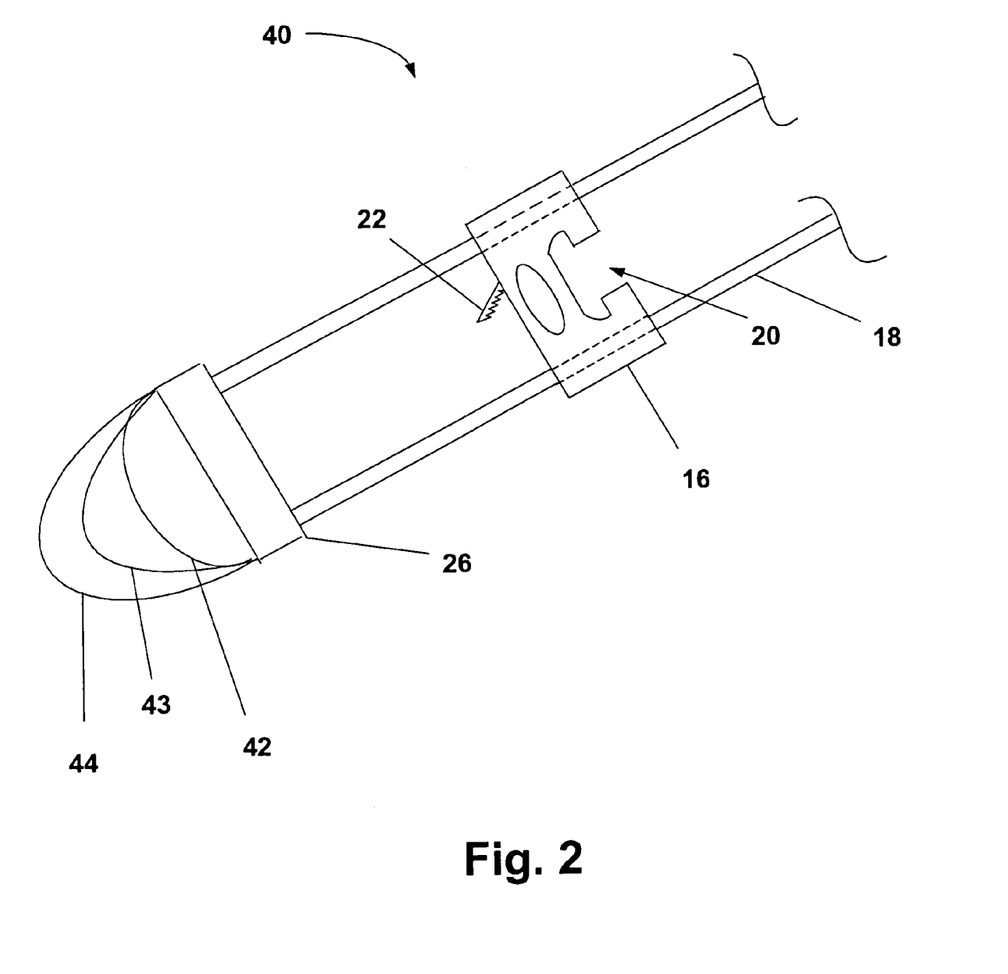
FIG. 2 shows a generalized view of a degassing tool according to another embodiment of the present invention.

A degassing tool 40 according to another embodiment of the present invention may be seen in FIG. 2. The embodiment of the invention shown in FIG. 2 is similar to the embodiment of the invention shown in FIG. 1 except that the locking mechanism is effected by a first loop 42, a second loop 43 and a third loop 44 that are hingedly, rotatably or otherwise moveably attached to the base 26. The first loop 42, the second loop 43 or the third loop 44 may be rotated about the base 26 to engage the latch 22, thereby maintaining the slide 16 in a fixed position. The different sizes of the first loop 42, the second loop 43 and the third loop 44 allow the slide 16 to be fixed into multiple positions. Additional locking loops may be implemented if desired to accommodate a plurality of locked positions for the slide.

Referring back to FIG. 1, use of the degassing tool 10 may include inserting a standard size syringe into the holder 12. A plunger of the syringe may be positioned into the plunger aperture 20 of the slide 16. The handle aperture 32 of the slide 16 may be grabbed by a user to pull the plunger of the syringe back away from the barrel of the syringe that is prevented from moving by the holder 12. When the slide 16 is pulled back far enough, the latch 22 will engage the locking mechanism 28, thereby maintaining the position of the slide 16 and, consequently, the plunger of the syringe. Thus, a vacuum will be formed and maintained in the barrel of the syringe because the plunger is able to maintain its position after drawing a vacuum. Any fluid residing in the barrel of the syringe may then be degassed.

The degassing tool 10 may be made from a variety of materials. For example, the degassing tool 10 may be made from aluminum, stainless steel or from various types of plastics.

Figure 3:
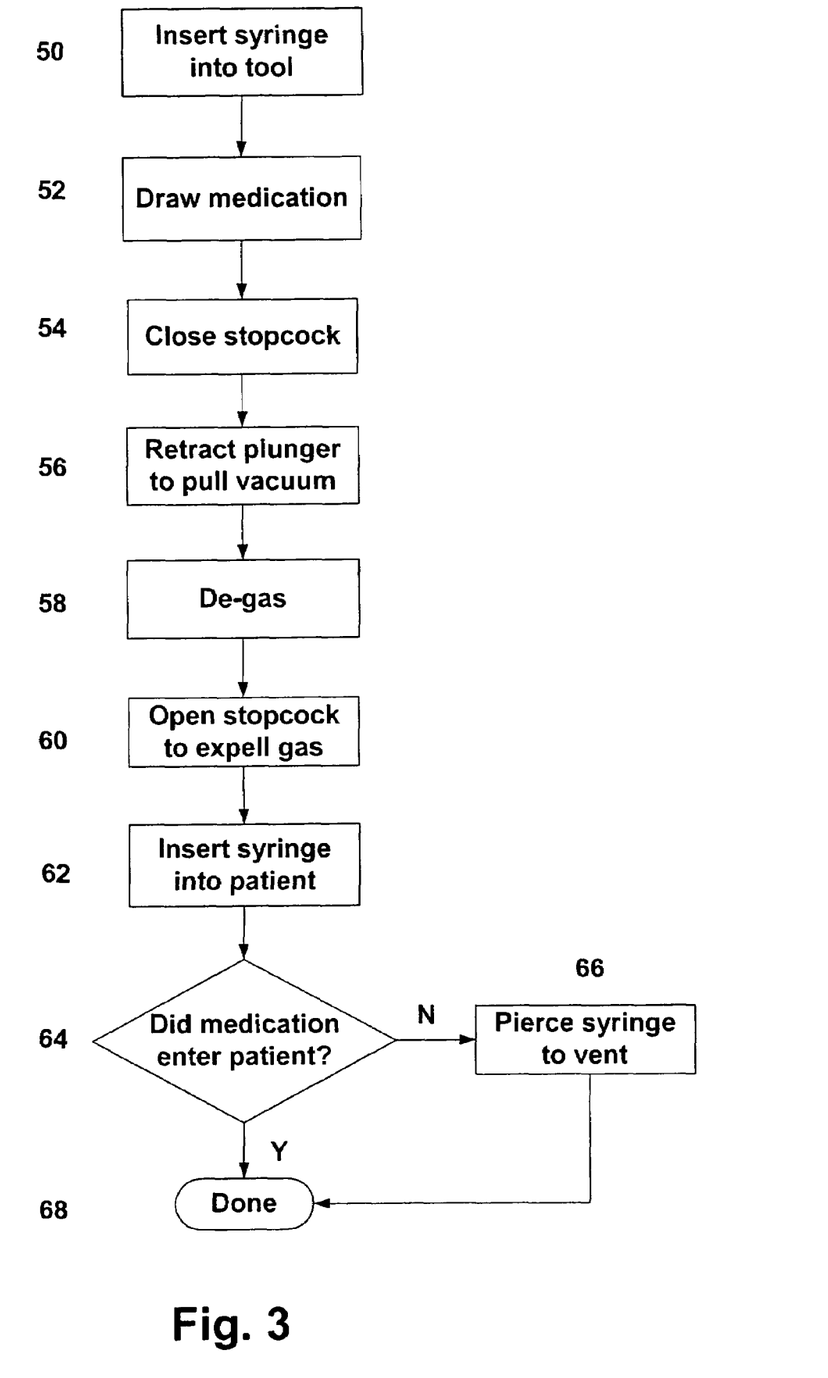
FIG. 3 shows a generalized method for using a degassing tool to degas a fluid and refill a negative pressure reservoir according to an embodiment of the present invention.

A generalized method of using a degassing tool to degas a fluid and refill a negative pressure reservoir according to an embodiment of the present invention is shown in FIG. 3. At step 50 a syringe is inserted into the tool. The syringe may be a standard size, off-the-shelf syringe common in the industry. At step 52, medication is drawn using a needle in the syringe such that the medication fills the barrel of the syringe. The medication may be insulin or some other fluid. Steps 50 and 52 may be interchanged if desired by the user.

At step 54, a stopcock may be used to close the syringe. At step 56, the plunger of the syringe may be retracted so that a vacuum is pulled in the barrel of the syringe. Thus, after step 56, the barrel of the syringe will include a fluid portion and a vacuous portion. Because the degassing tool may include a locking mechanism, the plunger may be locked into a fixed position, thereby maintaining the vacuum in the barrel of a syringe.

With a vacuum maintained in the barrel of the syringe, the medication or other fluid in the barrel may be degassed at step 58. Degassing of the medication or other fluid may be accomplished in a variety of ways. For example, according to an embodiment of the present invention, the entire syringe/degassing tool combination may be manually shaken by the user so that air or other gasses that have been dissolved in the medication or other fluid may be released into the vacuum. Shaking the syringe/degassing tool increases the amount of surface area of the fluid seen by the vacuum, thereby allowing a greater amount of gas to be expelled from the fluid into the vacuum.

Once the medication has been sufficiently degassed, the stopcock may be opened so that gasses residing in the previously evacuated area of the barrel of the syringe may be released through a needle in the syringe. If desired, steps 54 through 60 may be repeated to maximize the amount of degassing of the medication or other fluid. For example, according to an embodiment of the present invention, three cycles of steps 54 through 60 may be sufficient to adequately degas a fluid before injecting the fluid into a patient or a pump or reservoir implanted in a patient.

Subsequent to the last implementation of step 60, a needle in the syringe may be inserted into a negative pressure device implanted in the patient. The negative pressure device may be, for example, a pump, such as an insulin pump, for example, or other negative pressure reservoir. Because the implanted device is a negative pressure device, the fluid residing in the barrel of the syringe will normally enter the patient due to the prevailing, sufficiently greater pressure of the external environment. However, a query may be made at step 64. If the fluid entered the patient, the procedure is complete at step 68. If the fluid did not enter the patient, the syringe may be pierced by the piercing element so that air enters the barrel of the syringe and increases the pressure on the fluid in the barrel of the syringe. This should cause the fluid to enter the negative pressure device implanted into the patient.

Figure 4:
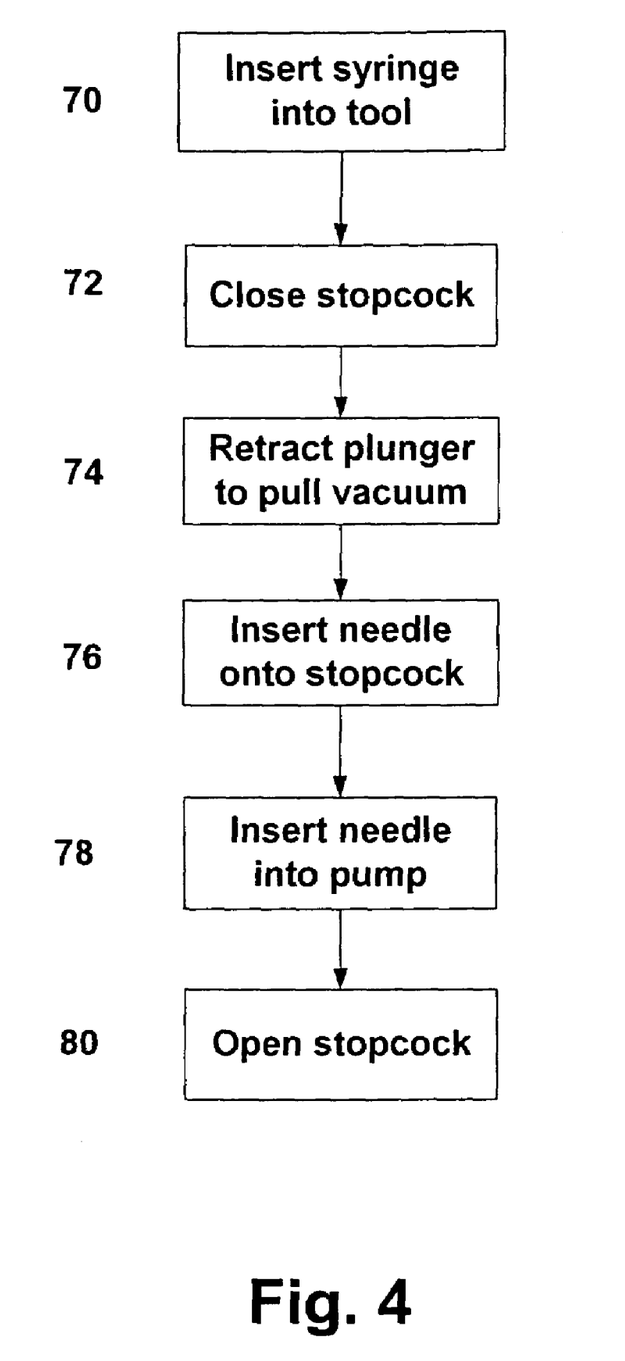
FIG. 4 shows generalized method for using a degassing tool to remove fluid from a negative pressure reservoir according to an embodiment of the present invention.

If fluid exists in the implanted device prior to degassing and filling/refilling the device, it may be desirable to remove the old fluid before filling the device with new fluid. A generalized method of using a degassing tool to remove fluid from a negative pressure device according to an embodiment of the present invention is shown in FIG. 4. At step 70, a syringe is inserted into a degassing tool such as, for example, the degassing tool shown in FIG. 1. At step 72, a stopcock may be inserted onto the syringe and closed to seal the syringe. At step 74, the plunger of the syringe may be retracted to pull a vacuum in the barrel of the syringe.

At step 76, a needle may be inserted onto the stopcock. At step 78, the needle is then inserted into the patient so that it makes contact with a fill/refill port on the implanted device. At this point, the pressure in the negative pressure device should be greater than that in the barrel of the syringe, which is at vacuum. Next, at step 80, the stopcock is opened and the fluid in the implanted device should flow freely into the barrel of the syringe.

Figure 5:
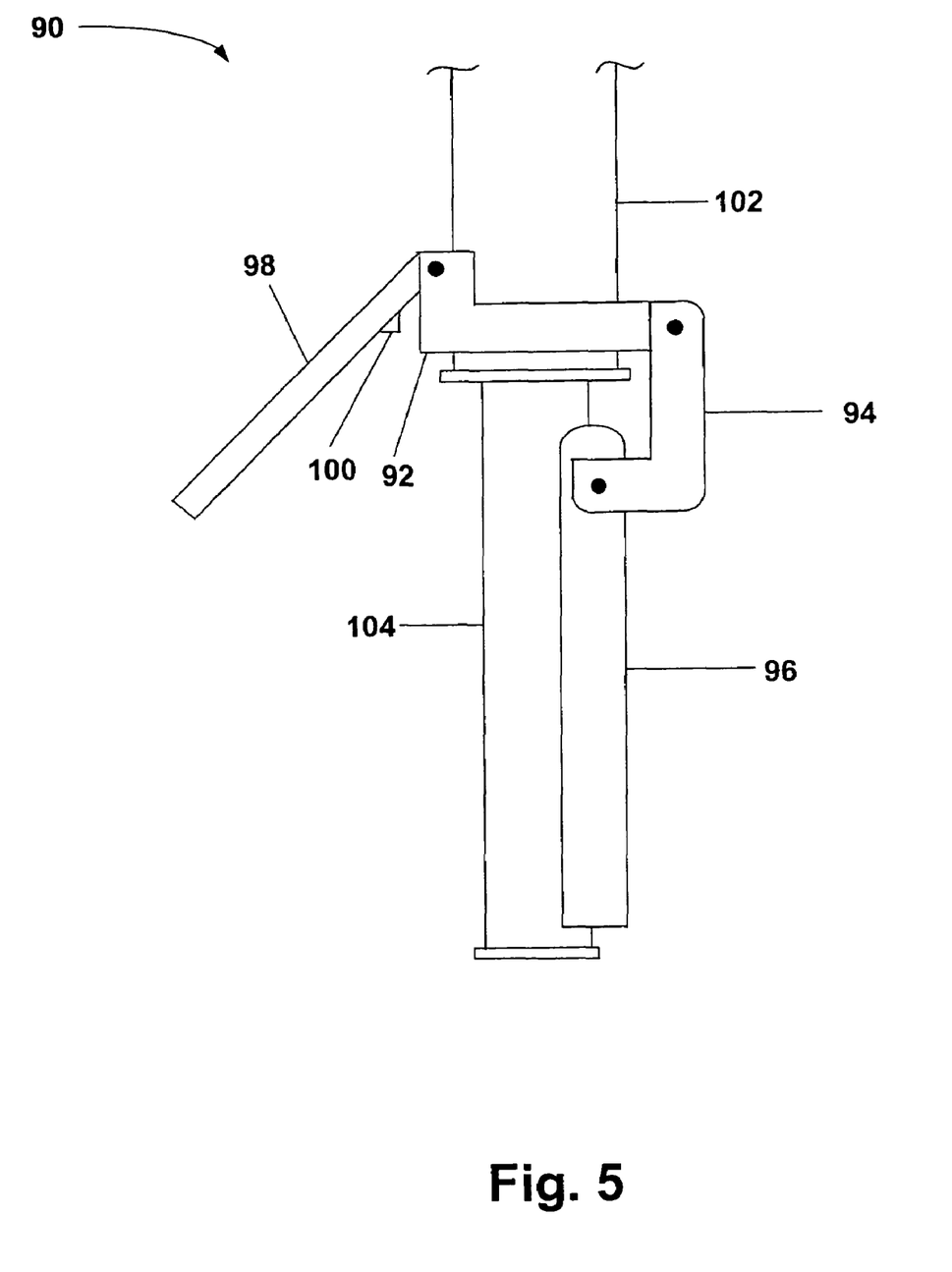
FIG. 5 shows a generalized view of a degassing tool according to another embodiment of the present invention.

A degassing tool 90 according to another embodiment of the present invention is shown in FIG. 5. The degassing tool 90 in FIG. 5 is shown with a syringe 102 having a plunger 104 inserted. The embodiment of the invention shown in FIG. 5 includes, but is not limited to a holder 92 for holding the syringe 102. Affixed to the holder 92 is an extension piece 94. The extension piece 94 may be hingedly or otherwise moveably attached to the holder 92.

Attached to the extension piece 94 is a locking post 96 which is hingedly or otherwise movably attached to the extension piece 94. The degassing tool 90 shown in FIG. 5 may also include a lever 98 and a piercing mechanism 100, similar to the lever and piercing mechanism shown in the embodiment of the invention of FIG. 1.

When using the embodiment of the invention shown in FIG. 5, the syringe 102 may be positioned into the holder 92. The plunger 104 may then be drawn back away from the holder 92 so that a vacuum is pulled within the barrel of the syringe 102. The extension piece 94 and the locking post 96, being hingedly or otherwise moveably attached to each other, and the extension piece 94 being hingedly or otherwise moveably attached to the holder 92, may be rotated away from the syringe and the plunger in order to draw the plunger 104 back. Once the plunger 104 has been drawn to the desired position, the extension piece 94 and the locking post 96 may be rotated toward the plunger 104 so that the locking post 96 prevents the plunger 104 from moving back into the barrel of the syringe 102. Thus, the vacuum pulled within the barrel of the syringe is maintained.

Figure 6A:
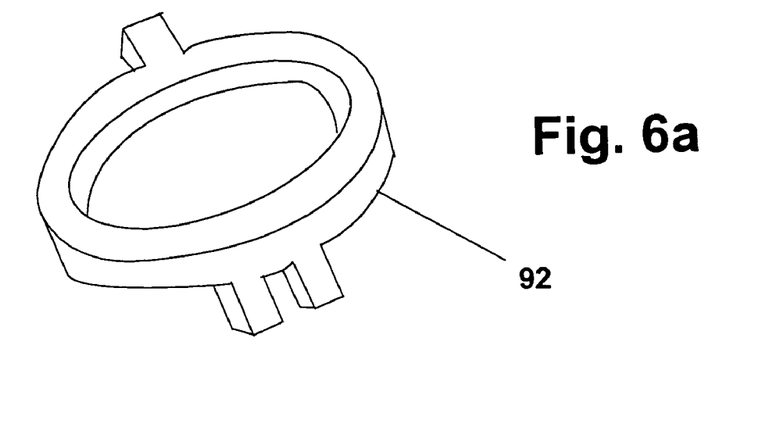
FIG. 6 shows a generalized view of components of the degassing tool shown in FIG. 5 according to another embodiment of the present invention.
Figure 6B:
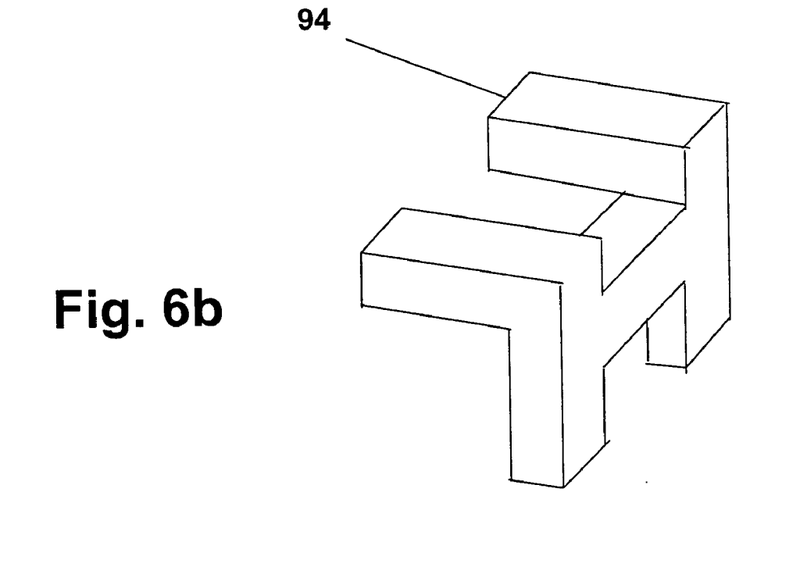

FIGS. 6a and 6b show perspective views of the holder 92 and the extension piece 94, respectively. The holder 92 may be sized and shaped to accept standard syringe sizes that are common in the industry. The extension piece 94, according to the embodiment of the invention shown at FIG. 6b, is formed as a "double L" shape to facilitate a moveable connection to the holder 92 and the locking post 96.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A system for degassing a fluid in a syringe comprising:
a holder for holding the syringe;
a guide affixed to the holder;
a slide for holding a plunger of the syringe, the slide being movably attached to the guide and moveable relative to the holder;
a locking mechanism for engaging the slide and maintaining a fixed position of the slide relative to the holder to inhibit movement of the plunger relative to the holder when the holder holds the syringe and the slide holds the plunger, and
a piercing element adjacent the holder for piercing the syringe;
wherein the fluid degasses when the locking mechanism maintains the fixed position of the slide relative to the holder.

2. The system of claim 1, wherein the holder is substantially circular.

3. The system of claim 1, wherein the holder accepts a barrel of the syringe.

4. The system of claim 1, wherein a size of the holder is adjustable.

5. The system of claim 1, wherein the guide is a cylindrical post.

6. The system of claim 1, wherein the guide comprises a first post and a second post.

7. The system of claim 6, wherein the slide comprises:
a first aperture for accepting the plunger of the syringe;
a second aperture adjacent the first aperture;
a third aperture on a first side of the slide for accepting the first post; and
a fourth aperture opposite the third aperture for accepting the second post.

8. The system of claim 1, wherein the guide comprises a single post.

9. The system of claim 8, wherein the slide rotates about the single post.

10. The system of claim 1, wherein the slide comprises:
a first aperture for accepting the plunger of the syringe;
a second aperture adjacent the first aperture;
a third aperture on a first side of the slide for accepting a first post; and
a fourth aperture opposite the third aperture for accepting a second post.

11. The system of claim 10, wherein the slide further comprises a latch for engaging the locking mechanism.

12. The system of claim 1, wherein a size of the slide is adjustable.

13. The system of claim 1, wherein the locking mechanism is spring loaded.

14. The system of claim 1, wherein the piercing element is movably attached to the holder, and
wherein a force applied to the piercing element forces the piercing element into the syringe.

15. The system of claim 1, wherein the piercing element pierces the syringe in a manner that precludes pieces of the syringe from separating from the syringe.

16. The system of claim 1, wherein the locking mechanism is supported in a fixed position relative to the holder by a support structure that is fixed relative to the holder.

17. The system of claim 1, further comprising a base supported in a fixed position relative to and spaced from the holder, wherein the locking mechanism is supported by the base and the slide is moveable between the holder and the base.

18. The system of claim 17, wherein the base is affixed to the guide.

19. A system for degassing a fluid in a syringe comprising:
a holder for holding the syringe;
a guide affixed to the holder;
a slide for holding a plunger of the syringe, the slide being movably attached to the guide; and
a locking mechanism opposite the holder for maintaining a position of the slide, wherein the fluid degasses when the locking mechanism maintains the position of the slide, further comprising a piercing element adjacent the holder for piercing the syringe, further comprising a lever hingedly attached to the holder,
wherein the piercing element is affixed to the lever,
wherein a rotational movement of the lever forces the piercing element into the syringe, and
wherein the piercing element peels away a portion of the syringe when the piercing element is forced into the syringe.

20. The system of claim 19, wherein the slide is movably attached between the locking mechanism and the holder.

21. A system for degassing a fluid in a syringe comprising:
a holder for holding the syringe;
a guide affixed to the holder;
a slide for holding a plunger of the syringe, the slide being movably attached to the guide;
a locking mechanism opposite the holder for engaging the slide and maintaining a position of the slide, and
a piercing element adjacent and moveably attached to the holder for piercing the syringe, wherein a force applied to the piercing element forces the piercing element into the syringe;
wherein the fluid degasses when the locking mechanism maintains the position of the slide,
wherein the slide is movably attached between the locking mechanism and the holder; and
wherein the piercing element peels away a portion of the syringe when the piercing element is forced into the syringe.

22. A degassing tool for degassing a fluid in a syringe comprising:
a holder for holding the syringe;
a guide affixed to the holder;
a slide for holding and moving a plunger of the syringe, the slide being movably attached to the guide; and
a piercing element adjacent the holder for piercing the syringe,
wherein the piercing element is affixed to a lever, the lever being affixed to the holder,
wherein a rotational movement of the lever forces the piercing element into the syringe at an angle transverse to the axis along which the plunger moves.

23. The degassing tool of claim 22, wherein the piercing element is movably attached to the holder, and
wherein a force applied to the piercing element forces the piercing element into the syringe.

24. The degassing tool of claim 22, wherein the piercing element pierces the syringe in a manner that precludes pieces of the syringe from separating from the syringe.

25. The degassing tool of claim 22, further comprising a locking mechanism disposed opposite the holder for maintaining a position of the slide.

26. The system of claim 25, wherein the locking mechanism is spring loaded.

27. The degassing tool of claim 22, wherein a rotational movement of the lever forces the piercing element into the syringe at an angle substantially perpendicular to the axis along which the plunger moves.

28. A method for making a system for degassing a fluid in a syringe comprising:
providing a holder for holding a syringe;
affixing a guide to the holder;
configuring a slide to hold a plunger of a syringe and moveably attaching the slide to the guide; and
providing a locking mechanism opposite the holder for maintaining a position of the slide to degasses fluid from the syringe,
further providing a piercing element adjacent the holder for piercing the syringe, and
configuring the piercing element to enter the syringe at an angle transverse to the axis along which the plunger moves.

29. The method of claim 28, wherein providing a holder comprises providing a holder that is substantially circular.

30. The method of claim 28, wherein providing a holder comprises configuring a holder to accepts a barrel of the syringe.

31. The method of claim 28, wherein providing a holder comprises providing a holder having a size that is adjustable.

32. The method of claim 28, wherein affixing a guide comprises affixing a cylindrical post to the holder.

33. The method of claim 28, wherein affixing a guide comprises affixing a first post and a second post to the holder.

34. The method of claim 33, wherein configuring a slide comprises:
providing a first aperture for accepting a plunger of the syringe;
providing a second aperture adjacent the first aperture;
providing a third aperture on a first side of the slide for accepting the first post; and
providing a fourth aperture opposite the third aperture for accepting the second post.

35. The method of claim 28, wherein affixing a guide comprises affixing a single post to the holder.

36. The method of claim 35, wherein moveably attaching a slide comprises arranging the slide to rotate about the single post.

37. The method of claim 28, wherein configuring a slide comprises:
providing a first aperture for accepting a plunger of the syringe;
providing a second aperture adjacent the first aperture;
providing a third aperture on a first side of the slide for accepting a first post; and
providing a fourth aperture opposite the third aperture for accepting a second post.

38. The method of claim 37, wherein configuring a slide further comprises providing a latch for engaging the locking mechanism.

39. The method of claim 28, wherein configuring a slide comprises providing a slide that is adjustable in size.

40. The method of claim 28, wherein providing a locking mechanism comprises providing a spring loaded locking mechanism.

41. The method of claim 28, further configuring the slide to be movably attached between the locking mechanism and the holder.

42. The method of claim 41, further supporting the locking mechanism in a fixed position relative to the holder by a support structure that is fixed relative to the holder.

43. The method of claim 28, wherein configuring the piercing element to enter the syringe at an angle comprises configuring the piercing element to enter the syringe at an angle substantially perpendicular to the axis along which the plunger moves.

44. A method for making a system for degassing a fluid in a syringe comprising:
   providing a holder for holding a syringe;
   affixing a guide to the holder;
   configuring a slide to hold a plunger of a syringe and moveably attaching the slide to the guide;
   providing a locking mechanism opposite the holder for maintaining a position of the slide to degasses fluid from the syringe;
   providing a piercing element adjacent the holder for piercing the syringe; and
   providing a lever hingedly attached to the holder,
   wherein providing a piercing element comprises affixing the piercing element to the lever such that a rotational movement of the lever forces the piercing element into the syringe at an angle transverse to the axis along which the plunger moves.

45. The method of claim 44, further configuring the slide to be movably attached between the locking mechanism and the holder.

46. The method of claim 44, wherein affixing the piercing element to the lever comprises affixing the piercing element such that a rotational movement of the lever forces the piercing element into the syringe at an angle substantially perpendicular to the axis along which the plunger moves.

* * * * *